United States Patent
Dvorsky et al.

(10) Patent No.: US 9,289,550 B1
(45) Date of Patent: *Mar. 22, 2016

(54) APPARATUS AND METHOD FOR DETECTING FLUID EXTRAVASATION

(75) Inventors: James E. Dvorsky, Plain City, OH (US); Chad E. Bouton, Delaware, OH (US); Alan D. Hirschman, Glenshaw, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 862 days.

This patent is subject to a terminal disclaimer.

(21) Appl. No.: 11/385,448

(22) Filed: Mar. 20, 2006

Related U.S. Application Data

(62) Division of application No. 10/060,561, filed on Jan. 30, 2002, now Pat. No. 7,047,058.

(60) Provisional application No. 60/266,710, filed on Feb. 6, 2001.

(51) Int. Cl.
*A61B 6/00* (2006.01)
*A61M 5/168* (2006.01)
*A61B 5/03* (2006.01)
(Continued)

(52) U.S. Cl.
CPC .............. *A61M 5/16836* (2013.01); *A61B 5/03* (2013.01); *A61B 5/0507* (2013.01); *A61B 5/4878* (2013.01); *G01N 22/00* (2013.01); *A61B 2562/04* (2013.01); *Y10S 128/13* (2013.01)

(58) Field of Classification Search
CPC .................. A61M 2005/172; A61M 5/16836; A61M 2005/1588; A61M 5/007; A61M 2205/3375; A61M 2205/3313; A61M 2005/1726; A61B 2562/04; A61B 5/4878; A61B 5/0507; A61B 5/03; G01N 22/00; Y10S 128/13

See application file for complete search history.

(56) References Cited

U.S. PATENT DOCUMENTS 3,779,079 A 12/1973 Snook
3,951,136 A 4/1976 Wall
(Continued)

FOREIGN PATENT DOCUMENTS

CA 2470801 2/2003
CN 100482151 C 4/2009
(Continued)

OTHER PUBLICATIONS

P. B. James and R. W. Galloway. The ultrasonic blood velocity detector as an aid to arteriography. Br J Radiol Oct. 1971 44:743-746.*
(Continued)

*Primary Examiner* — Long V Le
*Assistant Examiner* — Helene Bor
(74) *Attorney, Agent, or Firm* — Joseph L. Kent; David Schramm; James R. Stevenson

(57) ABSTRACT

An apparatus for the detection of extravasation of an injection fluid infused into a tissue during an imaging procedure is disclosed. The apparatus includes at least a first source of energy to supply an X-ray or gamma ray imaging energy to tissue in the vicinity of a site and at least a first sensor to measure an energy signal resulting from the energy supplied to the tissue by the first imaging energy source, and circuitry configured to compare the energy signal detected by the first sensor to a baseline measurement and provide an alert that extravasation is occurring.

12 Claims, 2 Drawing Sheets

(51) Int. Cl.
  *A61B 5/05* (2006.01)
  *A61B 5/00* (2006.01)
  *G01N 22/00* (2006.01)

(56) References Cited

U.S. PATENT DOCUMENTS

| | | | |
|---|---|---|---|
| 4,010,749 A * | 3/1977 | Shaw | 604/503 |
| 4,240,445 A | 12/1980 | Iskander et al. | |
| 4,329,689 A | 5/1982 | Yee | |
| 4,378,808 A | 4/1983 | Lichtenstein | |
| 4,488,559 A | 12/1984 | Iskander | |
| 4,572,182 A | 2/1986 | Royse | |
| 4,575,705 A | 3/1986 | Gotcher | |
| 4,637,929 A * | 1/1987 | Quay | 424/9.365 |
| 4,641,659 A | 2/1987 | Sepponen | |
| 4,647,281 A | 3/1987 | Carr | |
| 4,648,869 A | 3/1987 | Bobo, Jr. | |
| 4,653,501 A | 3/1987 | Cartmell et al. | |
| 4,667,679 A | 5/1987 | Sahota | |
| 4,690,149 A | 9/1987 | Ko | |
| 4,816,019 A | 3/1989 | Kamen | |
| 4,819,648 A | 4/1989 | Ko | |
| 4,877,034 A | 10/1989 | Atkins et al. | |
| 4,923,442 A | 5/1990 | Segall et al. | |
| 4,959,050 A | 9/1990 | Bobo, Jr. | |
| 4,971,068 A | 11/1990 | Sahi | |
| 4,993,409 A * | 2/1991 | Grim | 602/19 |
| 5,001,436 A | 3/1991 | Scot et al. | |
| 5,026,348 A | 6/1991 | Venegas | |
| 5,184,620 A | 2/1993 | Cudahy et al. | |
| 5,191,795 A | 3/1993 | Fellingham et al. | |
| 5,255,683 A | 10/1993 | Monaghan | |
| 5,334,141 A | 8/1994 | Carr et al. | |
| 5,479,927 A * | 1/1996 | Shmulewitz | 600/445 |
| 5,628,322 A | 5/1997 | Mine | |
| 5,685,305 A * | 11/1997 | Moonen et al. | 600/419 |
| 5,769,784 A | 6/1998 | Barnett et al. | |
| 5,840,026 A | 11/1998 | Uber, III et al. | |
| 5,861,019 A | 1/1999 | Sun et al. | |
| 5,947,910 A | 9/1999 | Zimmet | |
| 5,954,668 A * | 9/1999 | Uber et al. | 600/549 |
| 5,957,950 A | 9/1999 | Mockros et al. | |
| 5,964,703 A | 10/1999 | Goodman et al. | |
| 5,995,863 A | 11/1999 | Farace et al. | |
| 6,026,173 A | 2/2000 | Svenson et al. | |
| 6,031,892 A | 2/2000 | Karellas | |
| 6,047,215 A | 4/2000 | McClure et al. | |
| 6,061,589 A | 5/2000 | Bridges et al. | |
| 6,233,479 B1 | 5/2001 | Haddad et al. | |
| 6,263,226 B1 | 7/2001 | Axelgaard et al. | |
| 6,300,906 B1 | 10/2001 | Rawnick et al. | |
| 6,315,719 B1 | 11/2001 | Rode et al. | |
| 6,332,087 B1 | 12/2001 | Svenson et al. | |
| 6,375,624 B1 | 4/2002 | Uber, III et al. | |
| 6,385,483 B1 | 5/2002 | Uber, III et al. | |
| 6,397,098 B1 | 5/2002 | Uber, III et al. | |
| 6,408,204 B1 | 6/2002 | Hirschman | |
| 6,415,170 B1 | 7/2002 | Loutis et al. | |
| 6,425,878 B1 | 7/2002 | Shekalm | |
| 6,454,711 B1 | 9/2002 | Haddad et al. | |
| 6,459,931 B1 | 10/2002 | Hirschman | |
| 6,487,428 B1 * | 11/2002 | Culver et al. | 600/310 |
| 6,520,930 B2 | 2/2003 | Critchlow et al. | |
| 6,673,033 B1 | 1/2004 | Sciulli et al. | |
| 6,704,592 B1 | 3/2004 | Reynolds et al. | |
| 6,751,500 B2 | 6/2004 | Hirschman | |
| 6,970,735 B2 | 11/2005 | Uber, III et al. | |
| 7,047,058 B1 | 5/2006 | Dvorsky et al. | |
| 7,122,012 B2 | 10/2006 | Bouton et al. | |
| 7,221,159 B2 | 5/2007 | Griffiths et al. | |
| 7,283,860 B2 | 10/2007 | Frazier et al. | |
| 7,431,728 B2 | 10/2008 | Gerry et al. | |
| 7,457,804 B2 | 11/2008 | Uber, III et al. | |
| 7,591,792 B2 | 9/2009 | Bouton | |
| 7,627,710 B1 | 12/2009 | Todd et al. | |
| 7,632,245 B1 | 12/2009 | Cowan et al. | |
| 7,674,244 B2 | 3/2010 | Kalafut et al. | |
| 7,713,239 B2 | 5/2010 | Uber, III et al. | |
| 7,937,134 B2 | 5/2011 | Uber et al. | |
| 7,996,381 B2 | 8/2011 | Uber, III et al. | |
| 8,055,328 B2 | 11/2011 | Uber, III et al. | |
| 8,160,679 B2 | 4/2012 | Uber et al. | |
| 8,182,444 B2 | 5/2012 | Uber, III et al. | |
| 8,192,397 B2 | 6/2012 | Griffiths et al. | |
| 8,295,920 B2 | 10/2012 | Bouton et al. | |
| 8,307,693 B2 | 11/2012 | Uram et al. | |
| 8,323,240 B2 | 12/2012 | Wulfman et al. | |
| 8,352,015 B2 | 1/2013 | Bernstein et al. | |
| 8,388,582 B2 | 3/2013 | Eubanks et al. | |
| 8,454,561 B2 | 6/2013 | Uber, III et al. | |
| 8,521,716 B2 | 8/2013 | Uber, III et al. | |
| 2001/0044588 A1 | 11/2001 | Mault | |
| 2002/0040193 A1 | 4/2002 | Hirschman | |
| 2002/0123674 A1 | 9/2002 | Plicchi et al. | |
| 2002/0172323 A1 * | 11/2002 | Karellas et al. | 378/51 |
| 2003/0004433 A1 | 1/2003 | Hirschman | |
| 2003/0036674 A1 | 2/2003 | Bouton | |
| 2003/0036713 A1 | 2/2003 | Bouton et al. | |
| 2004/0162488 A1 | 8/2004 | Uber, III et al. | |
| 2006/0135884 A1 | 6/2006 | Hack et al. | |
| 2006/0213249 A1 | 9/2006 | Uram et al. | |
| 2007/0056871 A1 | 3/2007 | Griffiths et al. | |
| 2007/0123770 A1 | 5/2007 | Bouton et al. | |
| 2007/0225601 A1 | 9/2007 | Uber, III et al. | |
| 2007/0244428 A1 | 10/2007 | Uram et al. | |
| 2007/0276327 A1 | 11/2007 | Kalafut et al. | |
| 2007/0282198 A1 | 12/2007 | Uber, III et al. | |
| 2007/0282199 A1 | 12/2007 | Uber, III et al. | |
| 2008/0058758 A1 | 3/2008 | Ranchod et al. | |
| 2008/0097339 A1 | 4/2008 | Ranchod et al. | |
| 2008/0166292 A1 | 7/2008 | Levin et al. | |
| 2008/0167900 A1 | 7/2008 | Ranchod | |
| 2008/0195060 A1 | 8/2008 | Roger et al. | |
| 2008/0294096 A1 | 11/2008 | Uber, III et al. | |
| 2009/0070342 A1 | 3/2009 | Uber, III et al. | |
| 2009/0177050 A1 | 7/2009 | Griffiths et al. | |
| 2009/0247866 A1 | 10/2009 | Uber, III et al. | |
| 2009/0276327 A1 | 11/2009 | Malik | |
| 2009/0299175 A1 | 12/2009 | Bernstein et al. | |
| 2009/0326370 A1 | 12/2009 | Uber, III et al. | |
| 2010/0113887 A1 | 5/2010 | Kalafut et al. | |
| 2010/0114064 A1 | 5/2010 | Kalafut et al. | |
| 2010/0174179 A1 | 7/2010 | Persson et al. | |
| 2010/0185040 A1 | 7/2010 | Uber, III et al. | |
| 2010/0198141 A1 | 8/2010 | Laitenberger et al. | |
| 2011/0002802 A1 | 1/2011 | Capone et al. | |
| 2011/0130800 A1 | 6/2011 | Weinstein et al. | |
| 2011/0257522 A1 | 10/2011 | Berard-Andersen et al. | |
| 2013/0062528 A1 | 3/2013 | Hyde et al. | |
| 2013/0079581 A1 | 3/2013 | Agamaite et al. | |
| 2013/0123567 A1 | 5/2013 | Agamaite et al. | |
| 2013/0123614 A1 | 5/2013 | Bernstein et al. | |
| 2013/0131585 A1 | 5/2013 | Eubanks et al. | |
| 2013/0190646 A1 | 7/2013 | Weinstein et al. | |
| 2013/0231550 A1 | 9/2013 | Weinstein et al. | |
| 2013/0253254 A1 | 9/2013 | Uber, III et al. | |
| 2013/0255390 A1 | 10/2013 | Riley et al. | |
| 2013/0331634 A1 | 12/2013 | Kaintz et al. | |
| 2013/0331635 A1 | 12/2013 | Hoffman et al. | |
| 2013/0331810 A1 | 12/2013 | Bazala et al. | |
| 2013/0345676 A1 | 12/2013 | Wulfman et al. | |
| 2014/0046295 A1 | 2/2014 | Uber, III et al. | |
| 2014/0228686 A1 | 8/2014 | Bouton | |

FOREIGN PATENT DOCUMENTS

| | | |
|---|---|---|
| DE | 4007587 | 9/1991 |
| EP | 1472973 | 11/2004 |
| EP | 1647306 | 4/2006 |
| EP | 1675506 | 6/2010 |
| EP | 2455402 | 5/2012 |
| EP | 2526857 A3 | 4/2013 |
| EP | 2750594 | 7/2014 |
| EP | 2750595 | 7/2014 |

(56) References Cited

FOREIGN PATENT DOCUMENTS

| | | |
|---|---|---|
| GB | 2251080 | 6/1992 |
| JP | 11-57001 | 3/1999 |
| JP | 2007509353 A | 4/2007 |
| WO | WO 99/26685 | 6/1999 |
| WO | WO 99/26686 | 6/1999 |
| WO | WO 99/29356 | 6/1999 |
| WO | WO 01/08729 | 2/2001 |
| WO | 03009752 | 2/2003 |
| WO | 03009753 A2 | 2/2003 |
| WO | WO 03/000972 | 2/2003 |
| WO | 03063680 A2 | 8/2003 |
| WO | 2004036467 | 4/2004 |
| WO | 2005043100 A2 | 5/2005 |
| WO | 2008100670 | 8/2008 |
| WO | 2009009753 | 1/2009 |
| WO | 2010146372 | 12/2010 |
| WO | 2011067623 | 6/2011 |
| WO | 2011067685 | 6/2011 |
| WO | 2012011065 | 1/2012 |
| WO | 2012011066 | 1/2012 |
| WO | 2012059929 | 5/2012 |
| WO | 2013033162 A1 | 3/2013 |
| WO | 2013033166 A1 | 3/2013 |
| WO | 2013033174 A1 | 3/2013 |
| WO | 2013093923 | 6/2013 |
| WO | 2013147799 | 10/2013 |

OTHER PUBLICATIONS

"Value of Multi-Detector Array CT in the Assessment of Portal Hypertension." Portal Hypertension: Diagnostic Imaging and Imaging-guided Therapy (Medical Radiology/Diagnostic Imaging). Ed. Plinio Rossi. 1$^{st}$ ed. Springer, 2000: p. 111.*
Carr, K.L., "Use of Gallium Arsenide in Medical Applicatgions" IEEE Gallium Arsenide Integrated Circuits (GAAS IC) Symposium, vol. SYMP17, pp. 10-13, New York (Oct. 29, 1995).
Shaeffer, J. et al., "Early Detection of Extravastion of Radiographic Contrast Medium," Radiology, vol. 184, No. 1, pp. 141-144(Jul. 1992).
Shaeffer, James et al.; Detection of Extravasation of Antineoplastic Drugs by Microwave Radiometry; Cancer Letter, 31; pp. 284-291; 1986; Elsevier Scientific Publishers Ireland Ltd.
Sukamto, Lin M. et al.; MMIC Receiver for Water-Vapor Radiometer; NASA Tech Briefs; p. 34; Sep. 1993.
Arkin, H. et al.; Recent Developments in Modeling Heat Transfer in Blood Perfused Tissues; IEEE Transactions on Biomedical Engineering; vol. 41, No. 2; pp. 97-107; Feb. 1994.
Harris, Thomas S. et al.; Infusion Line Model for the Detection of Infiltration Extravasation, and other Fluid Flow Faults; IEEE Transactions on Biomedical Engineering; vol. 40, No. 2; pp. 154-162; Feb. 1993.
Montreuil, Jean et al.; Multiangle Method for Temperature Measurement of Biological Tissues by Microwave Radiometry; IEEE Transactions on Microwave Theory and Techniques; vol. 39, No. 7; pp. 1235-1238; Jul. 1991.
Lin, James C. et al.; Microwave Imaging of Cerebral Edema; Proceedings of the IEEE; vol. 70, No. 5; pp. 523-524; May 1982.
Kramer, Gerhard G. et al.; Dielectric Measurement of Cerebral Water Content Using a Network Analyzer; Neurological Research; vol. 14, No. 3; pp. 255-258; Sep. 1992.
Ling, Geoffrey S.F. et al.; Diagnosis of Subdural and Intraparenchymal Intracranial Hemorrhage Using a Microwave Based Detector; Digitization of the Battlespace V and Battlefield Biomedical Technologies II; vol. 4037; pp. 212-217; Apr. 24, 2000.
Behari, J. et al.; Dielectric Permittivity of Biological Tissues in the Microwave Frequency Range; Proceedings of the SPIE—The International Society for Optical Engineering, Advanced Microwave and Millimeter-Wave Detectors; vol. 2275; pp. 301-308; San Diego, CA; Jul. 25-26, 1994.
Andreuccetti, D. et al.; High Permittivity Patch Radiator for Single and Multi-Element Hyperthermia Applicators; IEEE Transactions on Biomedical Engineering; vol. 40, No. 7; pp. 711-715; IEEE Inc.; New York; Jul. 1, 1993.
Lee, Eric R. et al.; Body Conformable 915 MHz Microstrip Array Applicators for Large Surface Area Hyperthermia; IEEE Transactions on Biomedical Engineering; vol. 39, No. 5; pp. 470-438; IEEE Inc., New York; May 1, 1992.
Jameson, P.; International Search Report; Application No. PCT/US00/20112; Oct. 17, 2000; European Patent Office.
Van Dooren, G.; International Search Report; Application No. PCT/US02/23877; Feb. 6, 2003; European Patent Office.
Beitner, M.; International Search Report; Application No. PCT/US02/23925; Jan. 15, 2003; European Patent Office.
Birnbaum et al. "Extravasation Detection Accessory: Clinical Evaluation in 500 Patients" 1999, Radiology 212:431-438.
Kent "Hand-Held Instrument for Fat/Water Determination in Whole Fish" 1993, at http://distell.com/products/prd-fish-fatmeter/technical-data/ffm-research-paper.
European Search Report for EP12005361 dated Mar. 6, 2013.
Partial European Search Report for EP12005361 dated Nov. 2, 2012.
Supplementary European Search Report for EP04796177 dated May 11, 2010.
International Preliminary Report on Patentability and Written Opinion dated Oct. 5, 2005 for PCT/US2004/35135.
Bouton, Chad E.; Final Office Action; U.S. Appl. No. 13/620,310; Jan. 6, 2014; United States Patent and Trademark Office; Alexandria, VA.
International Search Report for PCT/US2004/035135 dated Oct. 5, 2005.
European Search Opinion for EP12005361 dated Mar. 6, 2013.
Chad E. Bouton; U.S. Appl. No. 14/241,179, filed Mar. 11, 2014 entitled Wireless and Power-Source-Free Extravasation and Infiltration Detection Sensor; United States Patent and Trademark Office; Alexandria, VA (National Stage of PCT/US2012/052801 filed Aug. 29, 2012).
De la Hera, German; International Search Report and Written Opinion; International Application No. PCT/US2012/052796; Dec. 10, 2012; European Patent Office.
De la Hera, German; International Search Report and Written Opinion; International Application No. PCT/US2012/052801; Dec. 19, 2012; European Patent Office.
De la Hera, German; International Search Report and Written Opinion; International Application No. PCT/US2012/052813; Dec. 7, 2012; European Patent Office.
Chad E. Bouton; U.S. Appl. No. 14/241,171, filed Mar. 11, 2014 entitled Distributed Extravasation Detection System; United States Patent and Trademark Office; Alexandria, VA (National Stage of PCT/US2012/052796 filed Aug. 29, 2012).

* cited by examiner

APPARATUS AND METHOD FOR DETECTING FLUID EXTRAVASATION

CROSS-REFERENCE TO RELATED APPLICATION

This application is a division of application Ser. No. 10/060,561, filed on Jan. 30, 2002 now U.S. Pat. No. 7,047,058, which claims priority to U.S. Provisional Application Ser. No. 60/266,710, filed on Feb. 6, 2001, the contents of which are hereby incorporated by reference

BACKGROUND OF THE INVENTION

The present invention relates generally to the detection of extravasation of fluids injected into a patient, and, more particularly, to extravasation detection apparatuses, systems and methods in medical injection procedures using energy transmission through tissue in the vicinity of an injection site or other site.

In many medical diagnostic and therapeutic procedures, a physician or other person injects a patient with a fluid. In recent years, a number of injector-actuated syringes and powered injectors for pressurized injection of contrast medium in procedures such as angiography, computed tomography, ultrasound and NMR/MRI have been developed.

Extravasation is the accidental infusion of an injection fluid such as a contrast medium into tissue surrounding a blood vessel rather than into the blood vessel itself. Extravasation can be caused, for example, by fragile vasculature, valve disease, inappropriate needle placement, or patient movement resulting in the infusing needle being pulled from the intended vessel or causing the needle to be pushed through the wall of the vessel. Furthermore, high injection pressures and/or rates of some modern procedures increase the risk of extravasation. In computed tomography, for example, contrast injection flow rates can be in the range of 0.1 to 10 ml/s.

Moreover, extravasation can cause serious injury to patients. In that regard, certain injection fluids such as contrast media or chemotherapy drugs can be toxic to tissue if not diluted by blood flow. It is, therefore, very important when performing fluid injections to detect extravasation as soon as possible and discontinue the injection upon detection.

Several extravasation techniques are known in the art. Two simple and very useful techniques for detecting extravasation are palpation of the patient in the vicinity of the injection site and simple visual observation of the vicinity of the injection site by a trained health care provider. In the palpation technique, the health care provider manually senses swelling of tissue near the injection resulting from extravasation. By visual observation, it is also sometimes possible to observe directly any swelling of the skin in the vicinity of an injection site resulting from extravasation.

In addition to palpation and observation, there are a number of automated methods of detecting extravasation that may include automatic triggering of an alarm condition upon detection. Unfortunately, each of these automated methods of detecting extravasation is limited by significant drawbacks.

U.S. Pat. No. 4,647,281, for example, discloses subcutaneous temperature sensing of extravasation to trigger an alarm. In this method of extravasation detection, an antenna and a microwave radiometer instantaneously measure the temperature of the subcutaneous tissue at the site where fluid is injected. An algorithm periodically determines the temperature difference between the tissue and the injected fluid, and compares the difference to a fixed threshold. An alarm processor uses the comparison to determine an alarm condition.

In addition, U.S. Pat. No. 5,334,141 discloses a microwave extravasation detection system employing a reusable microwave antenna and a disposable attachment element for releasably securing the microwave antenna to a patient's skin over an injection site. The attachment element holds the antenna in intimate contact with the patient's skin to optimize microwave transfer therebetween, while shielding the antenna from environmental noise signals. Although measurement of temperature changes and emissivity using microwave energy can result in instantaneous detection, temperature differences are often too small for practical measurement.

Several plethysmographic detection techniques are available in addition to known temperature sensing techniques. For example, mercury strain gauge plethysmographs measure the volume change resulting from venous blood flow in a cross-sectional area of a limb of a patient. Air cuff or pulse volume recorder plethysmographs measure the changes in pressure within a recording cuff caused by the change in volume of a limb or digit as a result of extravasation. Such plethysmographs can be cumbersome to operate and/or insensitive to small changes in volume.

Photo-plethysmographs measure the optical scattering properties of capillary blood to detect the presence of extravasated fluids in tissue. An example of a photo-plethysmograph is described in U.S. Pat. No. 4,877,034. Because light is heavily absorbed in tissue, however, the sensitivity of photo-plethysmographs is generally limited to the top ¼ inch to ½ inch of tissue. Most extravasations, however, occur deeper than ¼ inch to ½ inch. Moreover, the injection medium may flow into interstitial spaces remote from the photo-plethysmograph sensors and go undetected.

Impedance plethysmographs measure changes in the electrical impedance in a defined tissue volume of a limb. In this method, an impedance change of a certain level in the vicinity of the injection site is interpreted as being an extravasation. A change in impedance occurs during extravasation because injection fluid in the tissue of the patient changes both the volume and the electrical impedance properties of the tissue. Use of electrodes in impedance plethysmographs can, however, result in instabilities. For example, maintaining suitable electrical contact between the electrodes of impedance plethysmographs and the skin of the patient is often very difficult.

It is, therefore, very desirable to develop improved devices and methods for detecting extravasation during, for example, the high flow rate procedures (1 to 10 ml/sec) typically encountered in angiographic, CT, ultrasound, and MR imaging procedures.

SUMMARY OF THE INVENTION

Current automated methods for detecting extravasation do not take adequate advantage of the inherent or designed properties of the injection fluid. In the case of a contrast medium, for example, the contrast medium is designed to affect a certain type or types of applied energy (that is, the imaging energy) to provide an enhanced image of an internal region (sometimes referred to as a region of interest or ROI) of a patient. The inherent or designed properties of an injection medium can be used to provide a sensitive measurement of extravasation in real time.

In one embodiment, the present invention provides an apparatus for the detection of extravasation in an imaging procedure. Such imaging procedures typically include the steps of injecting a contrast medium into a patient and supplying imaging energy from a first source of imaging energy to a region of interest of the patient to create an image of the region of interest. As discussed above, this image is enhanced by the effect the contrast medium has upon the imaging energy in the region of interest. In general, the extravasation detection apparatus includes at least a second source of imaging energy to supply imaging energy to tissue in the vicinity of a site. The apparatus also includes at least one sensor to measure a signal resulting from the imaging energy supplied to the tissue by the second imaging energy source.

The apparatus of the present invention thus uses the inherent or designed properties of the contrast medium to detect extravasation of the contrast medium. For example, in the case of a contrast medium designed to be use in connection with a procedure in which X-rays are used as the imaging energy (for example, computed tomography or CT), the contrast medium is designed to absorb, block or scatter transmission of X-rays and low energy gamma rays. In this embodiment, a source of X-rays or gamma rays preferably provides a safely low level of such energy to a site on a patient's limb at which extravasation is to be detected (for example, the injection site). An energy sensor or detector that is suitable for detecting X-rays and/or gamma rays is preferably positioned on an opposing side of the limb from the energy source. The level of energy detected by the sensor provides an instantaneous and sensitive measurement of extravasation.

Other energy sources can be used in the present invention depending upon the properties of the contrast medium. Ultrasound imaging, for example, creates images of the human body by broadcasting ultrasonic energy into the body and analyzing the reflected ultrasound energy. Differences in reflected energy (for example, amplitude or frequency) appear as differences in gray scale or color on the output images. As with other medical imaging procedures, contrast media can be injected into the body to increase the difference in the reflected energy and thereby increase the gray scale or color contrast displayed in the image (that is, the image contrast) viewed by the operator. These same properties of an ultrasound contrast medium used to enhance the imaging procedure can also be used to detect extravasation.

Preferably, the second imaging energy source and the sensor are positioned in a manner so that the vicinity of the site is available for palpation and visible for visual inspection. Unlike many other devices for automated detection of extravasation, the energy source(s) and the sensor(s) of the present invention need not be in contact with patient.

It is not necessary that the energy source used in the extravasation detection apparatus of the present invention deliver the same type of energy that is delivered to the region of interest to produce an enhanced image. Indeed, the extravasation detection apparatuses of the present invention are not limited to imaging procedures and can be used in any injection procedure in which there is a potential for extravasation. For example, any injection medium that will reflect, scatter and/or absorb a type of energy can be detected by the extravasation detection apparatuses of the present invention. In general, the presence of such injection media will change the strength of an energy signal that is supplied thereto. For example, any injection medium that contains heavy metal ions is capable of absorbing or scattering X-rays or low energy gamma rays. Such injection media are, for example, used as contrast media in magnetic resonance imaging as well as in CT.

The present invention thus provides a method of detecting extravasation of an injection medium including the steps of supplying energy to tissue in the vicinity of a site and measuring a resultant signal. The energy is preferably selected so that the injection medium will reflect, scatter and/or absorb the energy. Moreover, the energy is preferably chosen to penetrate beyond superficial tissue layers (for example, to a depth greater than ½ inch).

In the case of an injection medium that does not inherently reflect, scatter and/or absorb energy, an additive can be placed in the injection medium to act as an extravasation detection medium. For example, an ultrasound contrast agent can be added to a chemotherapy agent for detection using ultrasonic energy. The present invention thus further provides a method for detecting extravasation in an injection procedure in which an injection medium is injected into a patient that includes the steps of: mixing an additive with the injection medium; supplying energy to tissue in the vicinity of a site; and measuring a signal resulting from the energy supplied to the tissue. The additive is adapted to affect the signal so that extravasation is detectable.

The present invention further provides an injection system including a powered injector and an extravasation detection apparatus. The extravasation detection apparatus includes at least one source of energy to supply energy to tissue in the vicinity of a site and at least one sensor to measure a resultant signal. In general, the signal is proportionate to the energy reflected, scattered and/or absorbed by extravasated fluid in the vicinity of the site.

The present invention also provides an apparatus for the detection of extravasation including at least a first source of X-ray energy or gamma ray energy to supply X-ray energy or gamma ray energy and at least a first sensor to measure a signal resulting from the energy supplied to the tissue. Likewise, the present invention also provides an apparatus for the detection of extravasation including at least a first source of ultrasonic energy to supply ultrasonic energy and at least a first sensor to measure a signal resulting from the ultrasonic energy supplied to the tissue.

The present invention also provides a method for detecting extravasation in an imaging procedure. As discussed above, the imaging procedure generally includes the steps of injecting a contrast medium into a patient and supplying imaging energy to a region of interest of the patient to enhance an image. The method of the present invention includes the steps of: supplying imaging energy to tissue in the vicinity of a site; and measuring a signal resulting from the imaging energy supplied to the tissue.

Likewise, the present invention provides a method for detecting extravasation including the steps of (1) supplying X-ray energy, gamma ray energy and/or ultrasonic energy to tissue in the vicinity of a site, and (2) measuring a signal resulting from the energy supplied to the tissue.

In some patients, extravasation sometimes occurs at a site remote from the catheter insertion point (that is, the injection site). The present invention easily affords the ability to detect extravasation at the injection site and/or any position or site remote from an injection site, but along a path of potential extravasation. Multiple energy sources and/or multiple sensors may be positioned along a path of potential extravasation.

Numerous other advantages are afforded by the apparatuses, systems and methods of the present invention as compared to current apparatuses, systems and methods of detecting extravasation. For example, a larger portion of tissue can be probed for the presence of extravasated injection fluid.

Unlike prior modalities, detection of extravasation in the present invention is not sensitive only in superficial layers of tissue, but can preferably reach through the entire tissue volume into which injection fluid can migrate in the case of extravasation.

Moreover, because contact with the patient is not required in the present invention, the detection site(s) remain open for visualization and/or palpation. Likewise, tight coupling of transducers to the patient's skin and attendant discomfort and/or tissue damage are avoided. The devices of the present invention can also be used in connection with multiple procedures and patients, eliminating the expense and operative inconvenience associated with disposable sensors used in other techniques.

The present invention and its attendant advantages will be further understood by reference to the following detailed description and the accompanying drawings.

DETAILED DESCRIPTION OF THE INVENTION

Figure 1:
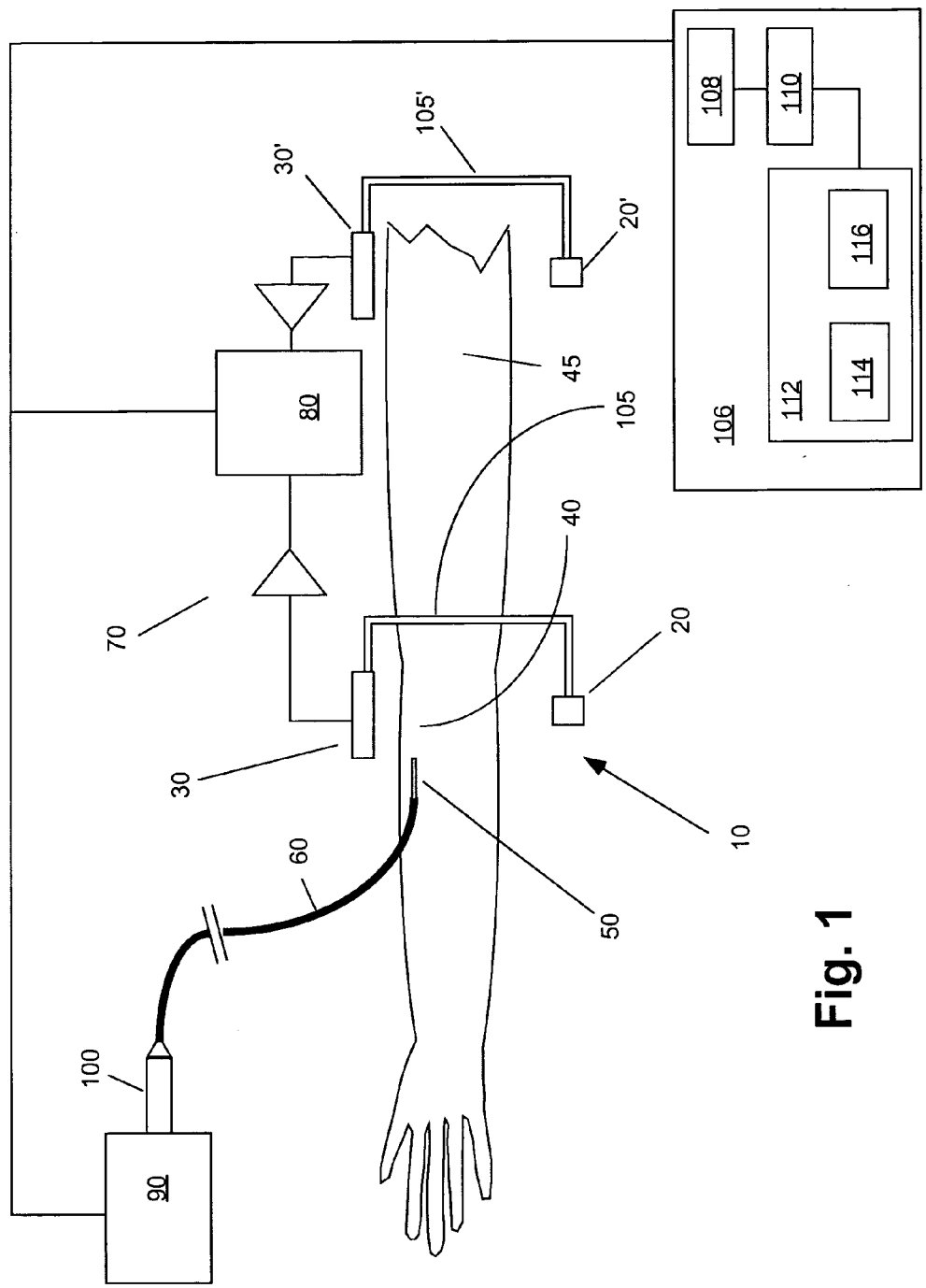
FIG. 1 illustrates a side view of an embodiment of a device or apparatus for detecting extravasation of the present invention.

FIG. 1 illustrates one embodiment of an extravasation detection apparatus or device 10 of the present invention. Extravasation detection device 10 preferably includes an energy source 20 that is preferably positioned on one side of a site at which extravasation is to be detected. A sensor 30 suitable to detect a signal resulting from transmission of the energy emitted by energy source 20 may be positioned opposite energy source 20 such that energy (for example, X-ray energy or gamma ray energy) that is emitted by energy source 20 and is transmitted through the tissue of a patient's limb 45 is detected by sensor 30.

In the case that reflected energy is to be measured (for example, in the case of ultrasound energy), energy source 20 and sensor 30 are preferably positioned on the same side of a site. In FIG. 1, energy source 20 and sensor 30 are positioned about an injection site 40 on a patient's limb 45 as defined by injection needle 50, which is connected to a source of injection fluid by a fluid path 60.

During an injection procedure, energy emitted by energy source 20 supplies energy to the tissue of limb 45, and a resultant signal is detected by sensor 30. Unlike prior extravasation detection systems, inherent or designed properties of the injection fluid may be used in the apparatus of the present invention to detect extravasation. For example, injection fluids such as contrast media used in imaging procedures are chosen or designed to respond in a particular manner to imaging energy. For example, the imaging energy may be transformed, reflected, scattered and/or absorbed by a contrast medium. It is this property of a contrast medium that enables enhancement of an image of a region of interest. These and other inherent properties of an injection medium (or an additive thereto) can be used to provide a sensitive detection of extravasation in real time.

Sensor 30 is preferably connected via circuitry 70 (as known in the art) to an alarm device 80 to provide an indication (for example, an audible, visible or tactile indication) to an operator that extravasation is occurring. Circuitry 70 can also be in communicative connection with a powered injector 90 used to pressurize injection fluid contained within a syringe 100 that is in fluid connection with fluid path 60.

Detection of extravasation can, for example, result in automatic cessation of the injection procedure by injector 90.

Extravasation device 10 can also be in communicative connection with an imaging system 106. Imaging system 106 may, for example, comprise a source of imaging energy 108 and a signal receiver 110. Receiver 110 is preferably in communicative connection with an imager 112 that may, for example, comprise a processing unit 114 and a display 116. Warning of extravasation can, for example, be displayed on display 116. A record of the occurrence of extravasation can also be maintained on a memory unit of processing unit 114 or another computer system.

Preferably, a fixed geometry is maintained between source 20, sensor 30 and site 40 to ensure consistent measurement. Source 20 and sensor 30 may, for example, be connected in a fixed relationship to each other by a frame 105 that can be positioned in a fixed manner relative to site 40.

Extravasation typically occurs in the immediate vicinity of the injection site. Extravasation may sometimes occur, however, at a site remote from the injection site 40. In the embodiment of FIG. 1, extravasation can be detected at a site remote from an injection site (but along a path of potential extravasation) using a second energy source 20' and a second sensor 30' that are preferably connected by a frame member 105'. Source 20' and sensor 30' operate as described above in connection with source 20 and sensor 30. Multiple energy source/sensor couplings of the present invention can be positioned as an array along a path of potential extravasation. It is thus possible to detect extravasation that may occur at remote locations as a result of injection of the fluid into the patient at the injection site.

Figure 2:
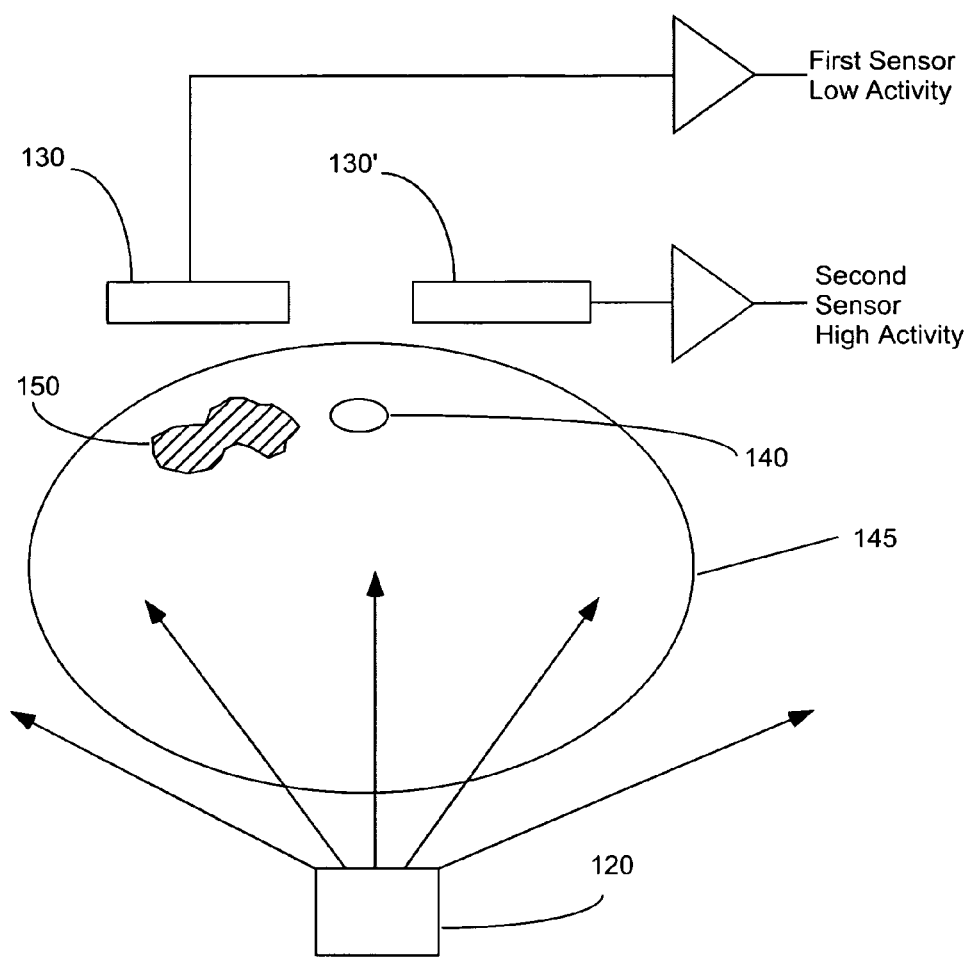
FIG. 2 illustrates another embodiment of a device or apparatus for detecting extravasation of the present invention.

The operation of one embodiment of the present invention will be discussed in further detail with reference to FIG. 2. In FIG. 2, a source 120 of, for example, low-level gamma rays (represented by arrows) is positioned opposite from sensors 130 and 130', each of which preferably includes a high-energy photonic detector. A patient's limb 145 is positioned between source 120 and sensors 130 and 130', which are positioned on each side of an artery 140.

Gamma ray source 120 can, for example, be any number of long half-life radioisotopes, such as Iodine-129 or Americium-241. Sensors 130 and 130' can, for example, include a photo multiplier tube, a solid-state detector (such as a cadmium-zinc-telluride or equivalent detector), or another gamma ray detector as known in the art.

Under conditions of no extravasation (as represented by the area on the right side of artery 140 in FIG. 2), gamma rays emitted from source 120 will pass through the limb and strike sensor 130'. Sensor 130' will register those gamma rays. Intervening tissue offers some resistance to the migration of high-energy photons, but this resistance is limited compared to the effect of the presence of contrast medium. Preferably, a baseline measurement is made before an injection procedure begins to account for the effect of intervening tissue on the energy. In the absence of extravasation, sensor 130' will register high activity (that is, generally equivalent to the baseline measurement).

When extravasation occurs, as represented by area to the left side of artery 140 in FIG. 2, contrast medium 150 "blocks" photons from striking sensor 130. Sensor 130 will, therefore, register measurably lower activity than the baseline measurement and an extravasation alarm can be indicated and/or the injection procedure automatically ended. A threshold value of change in activity from a baseline measurement is readily established to determine if extravasation has occurred.

Because contact with the patient's limb is not required in the present invention, the vicinity of the detection site is maintained in an unobstructed state for palpation and/or visual observation by health care providers.

Although the present invention has been described in detail in connection with the above embodiments and/or examples, it is to be understood that such detail is solely for that purpose and that those skilled in the art can make variations without departing from the invention. The scope of the invention is indicated by the following claims rather than by the foregoing description. All changes and variations that come within the meaning and range of equivalency of the claims are to be embraced within their scope.

What is claimed is:

1. An apparatus for detecting extravasation of an injection fluid infused into tissue, comprising:
    a first energy source emitting an energy, wherein the first energy source comprises a source of X-ray energy or gamma ray energy;
    a first sensor and at least a second sensor,
        wherein the first sensor detecting a resultant emitted energy after transmission, transformation, scattering, attenuation or absorption of the emitted energy supplied to the tissue by the first energy source, wherein a level of energy detected by the first sensor is related to extravasation, and
        wherein the at least a second sensor detecting the resultant emitted energy after transmission, transformation, scattering, attenuation or absorption of the emitted energy supplied to the tissue by the first energy source, wherein the level of energy detected by the second sensor is related to extravasation; and
    circuitry configured to compare the level of energy detected by the first sensor and the at least a second sensor to a baseline measurement, wherein the circuitry detects extravasation in real time with fluid injection when a threshold value of change in activity from the baseline measurement is detected in the level of energy detected by the at least a first sensor or the threshold value of change in activity from the baseline measurement is detected in the level of energy detected by the at least a second sensor and provides an alert that extravasation is occurring.

2. The apparatus of claim 1 wherein the first energy source, the first sensor, and the at least a second sensor are positioned in a manner so that a vicinity of an injection site is available for palpation and visible for visual inspection.

3. The apparatus of claim 1 wherein the first energy source, the first sensor, and the at least a second sensor do not contact the skin of a patient.

4. The apparatus of claim 1, wherein the energy is selected to reflect, scatter or absorb when transmitted through the tissue or the injection medium.

5. The apparatus of claim 1 wherein the at least a second sensor is capable of detecting high-energy photons.

6. The apparatus of claim 1 wherein the at least a second sensor is a high-energy photonic detector, photo multiplier tube, solid-state detector or gamma ray detector.

7. The apparatus of claim 1, further including an imaging apparatus to obtain an image of a region of interest.

8. A method for detecting extravasation, comprising:
    injecting at least an injection medium into a patient at a site;
    emitting a first energy from a first energy source comprising a source of X-ray energy or gamma ray energy to tissue in a vicinity of the site;
    measuring a first energy signal with a first sensor based on the first energy supplied to the tissue, wherein the first energy signal is related to a first energy reflected, scattered or absorbed by an extravasated fluid;
    measuring an at least a second energy signal with an at least a second sensor based on the first energy supplied to the tissue, wherein the at least a second energy signal is related to the first energy reflected, scattered or absorbed by the extravasated fluid; and
    comparing the first energy signal and the at least a second energy signal to a baseline measurement to detect extravasation in real time with injection of the injection medium.

9. The method of claim 8 further including supplying imaging energy from an imaging energy source to a region of interest of the patient to create an image.

10. The method of claim 9 in which the first energy and the imaging energy are substantially the same type.

11. The method of claim 8 wherein the injection includes an injection medium that transforms, reflects, scatters or absorbs the first energy supplied to the tissue.

12. An apparatus for detection of extravasation, the apparatus comprising:
    a first energy source to supply a first energy to tissue in a vicinity of a first site, wherein the first energy comprises x-ray energy or gamma ray energy;
    at least a first sensor to measure a resultant first energy signal resulting from the first energy supplied to the tissue by the first energy source at a first time;
    at least a second sensor to measure a resultant second energy signal resulting from the first energy supplied to the tissue by the first energy source at the first time; and
    circuitry configured to compare the resultant first energy signal and the resultant second energy signal to a baseline measurement, wherein the circuitry detects extravasation in real time with introduction of a fluid when a threshold value of change in activity from the baseline measurement is detected in the level of the resultant first energy signal detected by the first sensor or the threshold value of change in activity from the baseline measurement is detected in the level of the resultant second energy signal detected by the at least a second sensor and provides an alert that extravasation is occurring,
    wherein the resultant first energy signal is related to a first energy reflected, scattered or absorbed by an extravasated fluid; and
    wherein the resultant second energy signal is related to the first energy reflected, scattered or absorbed by the extravasated fluid.

* * * * *